(12) United States Patent
Afzali-Ardakani et al.

(10) Patent No.: US 8,969,118 B2
(45) Date of Patent: Mar. 3, 2015

(54) INTEGRATED CARBON NANOTUBE FIELD EFFECT TRANSISTOR AND NANOCHANNEL FOR SEQUENCING

(71) Applicant: International Business Machines Corporation, Armonk, NY (US)

(72) Inventors: Ali Afzali-Ardakani, Ossining, NY (US); Gustavo A. Stolovitzky, Riverdale, NY (US); Deqiang Wang, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 2 days.

(21) Appl. No.: 13/971,442

(22) Filed: Aug. 20, 2013

(65) Prior Publication Data

US 2014/0152330 A1    Jun. 5, 2014

Related U.S. Application Data

(63) Continuation of application No. 13/690,963, filed on Nov. 30, 2012.

(51) Int. Cl.
*H01L 21/00* (2006.01)
*G01N 27/414* (2006.01)
*B82Y 15/00* (2011.01)
*B82Y 30/00* (2011.01)
*G01N 27/02* (2006.01)
*G01N 33/487* (2006.01)

(52) U.S. Cl.
CPC ............ *G01N 27/4146* (2013.01); *B82Y 15/00* (2013.01); *B82Y 30/00* (2013.01); *G01N 27/02* (2013.01); *G01N 33/48721* (2013.01); *Y10S 977/958* (2013.01)
USPC ...................... 438/49; 257/E21.442; 977/958

(58) Field of Classification Search
CPC .................................................. H01L 21/02606
USPC ............................. 438/11, 962; 257/E21.442
See application file for complete search history.

(56) References Cited

U.S. PATENT DOCUMENTS 7,005,264 B2      2/2006 Su et al.
7,312,095 B1 *  12/2007 Gabriel et al. .................. 438/49
(Continued)

OTHER PUBLICATIONS

D. J. Branton et al., "The potential and challenges of nanopore sequencing," Nature biotechnology, vol. 26, No. 10, 2008, pp. 1146-1153.
(Continued)

*Primary Examiner* — Chandra Chaudhari
(74) *Attorney, Agent, or Firm* — Cantor Colburn LLP; Vazken Alexanian

(57) ABSTRACT

A mechanism is provided for base recognition of an integrated transistor and nanochannel. A target molecule is forced down to a carbon nanotube a single base at a time in the nanochannel by applying a gate voltage to a top electrode, and/or a narrow thickness of the nanochannel. The nanochannel exposes an exposed portion of the carbon nanotube at a bottom wall, and the top electrode is positioned over the exposed portion. The exposed portion of the carbon nanotube is smaller than the distance between bases to only accommodate the single base at a time. The target molecule is stretched by the narrow thickness and by applying a traverse voltage across a length direction of the nanochannel. The target molecule is frictionally restricted by the narrow thickness of the nanochannel to stretch is restrictedly translocates in the length direction. Current is measured to determine an identity of the single base.

16 Claims, 12 Drawing Sheets

(56) References Cited

U.S. PATENT DOCUMENTS

| | | | |
|---|---|---|---|
| 7,468,271 | B2 | 12/2008 | Golovchenko et al. |
| 7,736,943 | B2 * | 6/2010 | Tombler et al. ............... 438/100 |
| 8,000,903 | B1 * | 8/2011 | Li ................................... 702/22 |
| 2006/0246497 | A1 | 11/2006 | Huang et al. |
| 2009/0136958 | A1 | 5/2009 | Gershow et al. |
| 2011/0120868 | A1 | 5/2011 | Lindsay et al. |
| 2011/0279125 | A1 | 11/2011 | Bedell et al. |
| 2012/0073992 | A1 | 3/2012 | Kim et al. |

OTHER PUBLICATIONS

X. Chen et al., "Electrical Nanogap Devices for Biosensing," Materials Today, vol. 13, Issue 11, Nov. 2010, pp. 28-41.

Cherf et al. "Automated Forward and Reverse Ratcheting of DNA in a Nanopore at 5-A Precision," Nature Biotechnology, vol. 30, 2012, pp. 344-348.

Cees Dekker "Solid-state Nanopores," Nature Nanotechnology, vol. 2, 2007, pp. 209-215.

X. Guo et al., "Conductivity of a single DNA duplex bridging a carbon nanotube gap," Nature Nanotechnology, vol. 3, 2008, pp. 163—167.

X. Guo et al., "Covalently Bridging Gaps in Single-Walled Carbon Nanotubes with Conducting Molecules," Science, vol. 311, No. 5759, Jan. 20, 2006, pp. 356-359.

A. D. Franklin et al., "Device for Electrical Characterization of Molecules using CNT-Nanoparticle-MoleculeNanoparticle-CNT Structure," U.S. Appl. No. 13/674,492, filed Nov. 12, 2012.

* cited by examiner

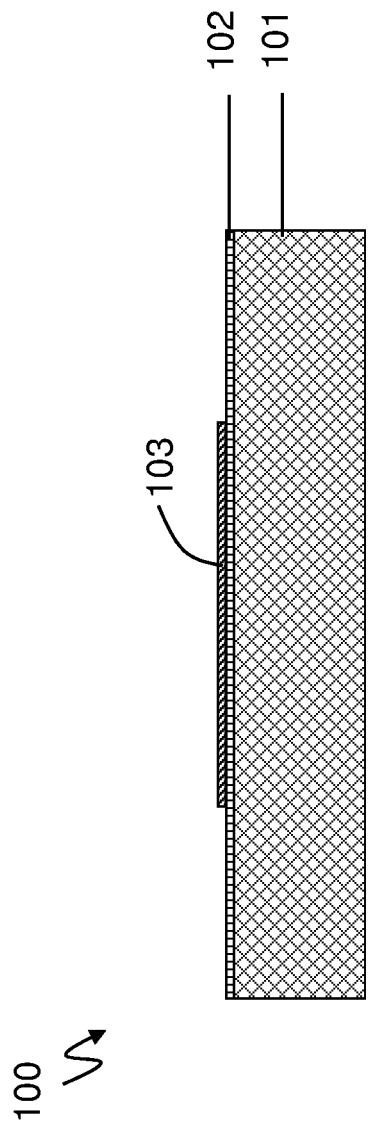

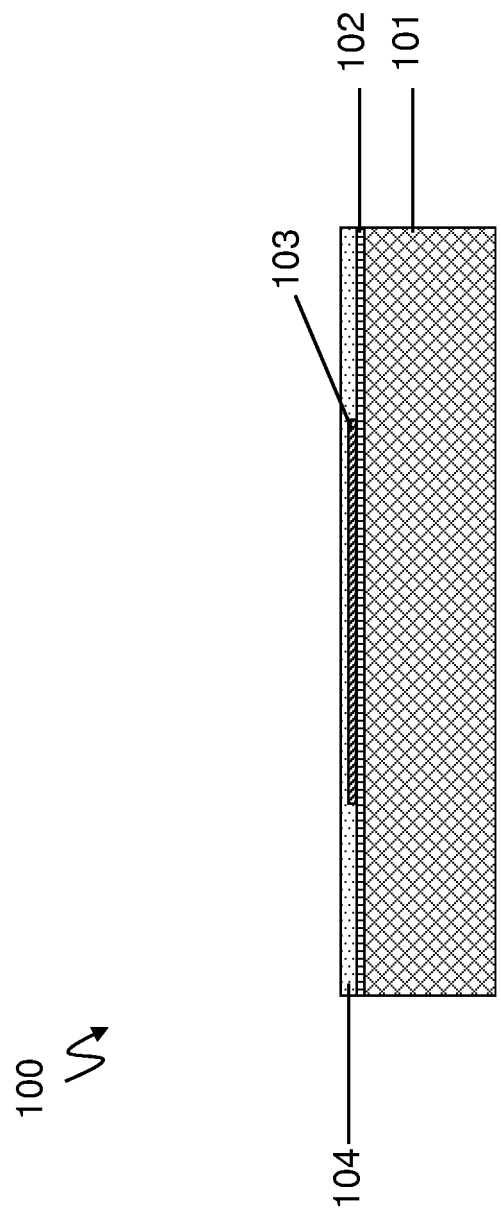

FIG. 4A

Force a target molecule down to a carbon nanotube a single base at a time in a nanochannel, the target molecule being forced to the carbon nanotube by applying a gate voltage to a top electrode of the transistor, and/or by a narrow thickness of the nanochannel 405

The nanochannel having been patterned over the carbon nanotube at an exposed portion of the carbon nanotube at a bottom wall of the carbon nanotube, the top electrode of the transistor positioned over the exposed portion of the carbon nanotube through nanochannel 410

The exposed portion of the carbon nanotube is smaller than a separating distance between bases on the target molecule, the exposed portion of the carbon nanotube being configured to only accommodate the single base at a time 415

Stretch the target molecule by the narrow thickness of the nanochannel and by applying a traverse voltage across a length direction of the nanochannel between a first electrode and a second electrode at opposite ends of the nanochannel in the length direction 420

The target molecule is frictionally restricted by the narrow thickness of the nanochannel causing the target molecule to stretch as the target molecule restrictedly translocates in the length direction while the traverse voltage is applied 425

Measure a transistor current while the single base of the target molecule is forced down to the exposed portion of the carbon nanotube in the nanochannel, the single base affecting the transistor current 430

Determine an identity of the single base according to a change in the transistor current while the single base is forced down to the exposed portion of the carbon nanotube in the nanochannel 435

INTEGRATED CARBON NANOTUBE FIELD EFFECT TRANSISTOR AND NANOCHANNEL FOR SEQUENCING

CROSS REFERENCE TO RELATED APPLICATIONS

The present application is a continuation of U.S. patent application Ser. No. 13/690,963, entitled "INTEGRATED CARBON NANOTUBE FIELD TRANSISTOR AND NANOCHANNEL FOR SEQUENCING", filed on Nov. 30, 2012, which is incorporated herein by reference in its entirety.

BACKGROUND

The present invention relates to nanodevices, and more specifically, to sequencing using an integrated carbon nanotube field effect transistor and nanochannel.

Nanopore sequencing is a method for determining the order in which nucleotides occur on a strand of deoxyribonucleic acid (DNA). A nanopore (also referred to a pore, nanochannel, hole, etc.) can be a small hole in the order of several nanometers in internal diameter. The theory behind nanopore sequencing is about what occurs when the nanopore is submerged in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods, so that the DNA might eventually pass through the nanopore. The scale of the nanopore can have the effect that the DNA may be forced through the hole as a long string, one base at a time, like thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome.

SUMMARY

According to an embodiment, a method for base recognition in an integration of a transistor and a nanochannel is provided. The method includes forcing a target molecule down to a carbon nanotube a single base at a time in the nanochannel. The target molecule is forced to the carbon nanotube by applying a gate voltage to a top electrode of the transistor, by a narrow thickness of the nanochannel, or both by applying the gate voltage to the top electrode of the transistor and by the narrow thickness of the nanochannel. The nanochannel having been patterned over the carbon nanotube exposes an exposed portion of the carbon nanotube at a bottom wall of the carbon nanotube, where the top electrode of the transistor is positioned over the exposed portion of the carbon nanotube through the nanochannel. The exposed portion of the carbon nanotube is smaller than a separating distance between bases on the target molecule, and the exposed portion of the carbon nanotube is configured to only accommodate the single base at a time. The target molecule is stretched by the narrow thickness of the nanochannel and by applying a traverse voltage across a length direction of the nanochannel between a first electrode and a second electrode at opposite ends of the nanochannel in the length direction. The target molecule is frictionally restricted by the narrow thickness of the nanochannel causing the target molecule to stretch as the target molecule restrictedly translocates in the length direction while the traverse voltage is applied. The method includes measuring a transistor current while the single base of the target molecule is forced down to the exposed portion of the carbon nanotube in the nanochannel. The single base affects the transistor current. The method includes determining an identity of the single base according to a change in the transistor current while the single base is forced down to the exposed portion of the carbon nanotube in the nanochannel.

According to an embodiment, a system for base recognition of a target molecule is provided. The system includes a transistor having a source electrode, a drain electrode, and a top electrode. The source electrode is electrically connected to the drain electrode by a carbon nanotube. A nanochannel is formed perpendicularly to the carbon nanotube and formed with a longitudinal direction extending away from the source electrode and the drain electrode. The nanochannel is formed of an insulating layer except at a single bottom location of the nanochannel. The single bottom location of the nanochannel is an exposed portion of the carbon nanotube, and the nanochannel is only formed of the carbon nanotube at the single bottom location. A size of the exposed portion of the carbon nanotube at the single bottom location is less than a separation distance between bases of the target molecule. The top electrode is positioned above the nanochannel to vertically line up to the exposed portion of the carbon nanotube at the single bottom location. The top electrode forces the target molecule down to the carbon nanotube a single base at a time in the nanochannel, and the target molecule is forced to the carbon nanotube by applying a gate voltage to the top electrode of the transistor and by a narrow thickness of the nanochannel. A transistor current is measured while the single base of the target molecule is forced down to the carbon nanotube in the nanochannel, so that the single base affects the transistor current. An identity of the single base is determined according to a change in the transistor current while the single base is forced down to the exposed portion of the carbon nanotube in the nanochannel.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIGS. 1A through 1E illustrate cross-sectional views of fabricating an integrated carbon nanotube field effect transistor (CNT-FET) and nanochannel device according to an embodiment, in which:

FIG. 1A is a cross-sectional view of the device with a carbon nanotube;

FIG. 1B is a cross-sectional view of an electrically insulating layer deposited on the surface of the device;

FIG. 1C is a cross-sectional view of a nanochannel or nanotrench formed through the insulating layer exposing the carbon nanotube;

FIG. 1D is a cross-sectional view of another electrically insulating layer deposited on the previous insulating layer to seal the nanochannel; and FIG. 1E is a cross-sectional view of the device with electrodes deposited.

FIGS. 4A and 4B together are a flow diagram illustrating a method for base recognition in a transistor and a nanochannel system according to an embodiment.

DETAILED DESCRIPTION

Figure 1C:
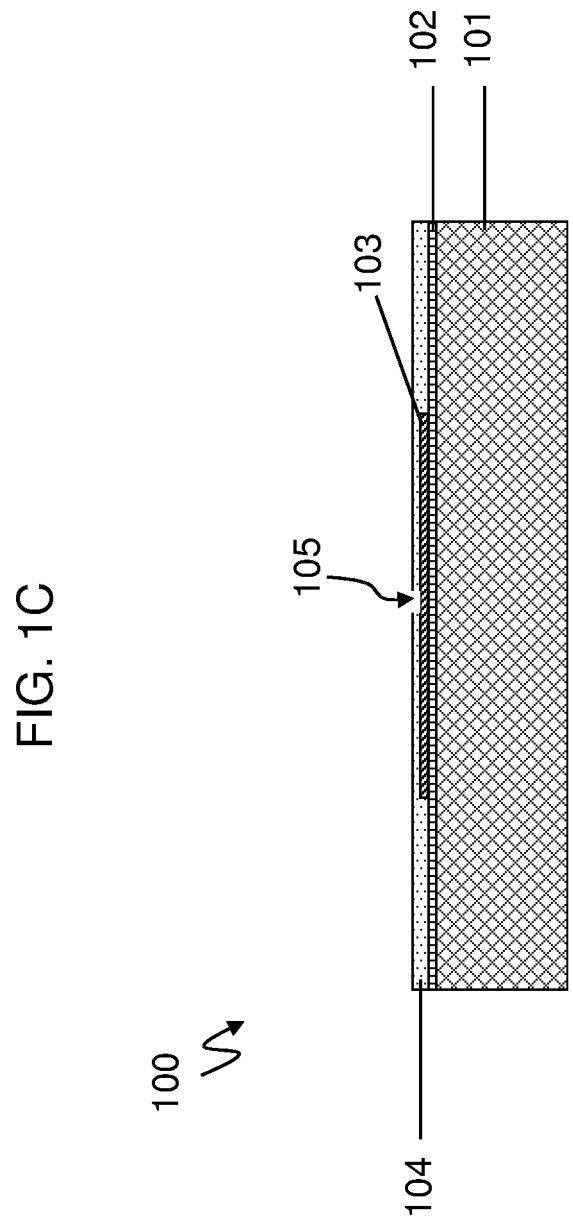

An embodiment of the present invention provides techniques to integrate the carbon nanotube field effect transistor (CNT-FET) and nanochannel for DNA/RNA sequencing. Single or double strand DNA/RNA can be pulled through the nanochannel which can confine the motion of DNA/RNA. The CNT-FET can read the nucleotide (i.e., base) information when the DNA/RNA moves over the carbon nanotube inside nanochannel. The DNA/RNA can be pulled down towards the carbon nanotube by a vertical electrical field. The DNA/RNA also can be stretched by the transverse electrical field and/or physical size of the interface between the carbon nanotube and the top sealing insulating film.

Currently, different state of the art methods are employed to control the trap, ratchet the long DNA/RNA, and sense single nucleotide information. Those methods may have their own advantages, but have not realized the DNA/RNA sequencing in low cost and short time with high accuracy. The embodiment utilizes the CNT-FET as a sensor to read the nucleotide information when the DNA/RNA is moving over the carbon nanotube. The nanochannel, vertical electrical field, and transverse electrical field can confine the conformation and movement of DNA/RNA in the nanochannel.

FIGS. 1A through 1E illustrate cross-sectional views of fabricating the integrated the carbon nanotube field effect transistor (CNT-FET) and nanochannel device 100 according to an embodiment. FIGS. 1A through 1E may be generally referred to as FIG. 1. FIG. 1 illustrates the processes to integrate the CNT-FET and nanochannel for DNA/RNA sequencing so that the bases of a target molecule being tested can be individually pressed to an exposed portion of the carbon nanotube.

FIG. 1A is a cross-sectional view of forming the multilayered device 100. The device 100 includes a substrate 101 which may be any electrically insulating substrate such as silicon. An electrically insulating film 102 is deposited on the substrate 101. The electrically insulating film 102 may be a dielectric material such as hafnium oxide. A carbon nanotube 103 is selectively placed on the surface of the electrically insulating film 102.

FIG. 1B illustrates that an electrically insulating film 104 which may be grown with atomic layer deposition to control the accuracy of thickness. The insulating film may be silicon dioxide, aluminum oxide, etc. The thickness of the electrically insulating film 102 can be a few to tens of nanometers, such as, e.g., 10 nm. The thickness of the electrically insulating film 104 can be, e.g., 3 to 5 nm.

FIG. 1C illustrates a nanochannel 105 (e.g., a nanotrench) formed through the insulating film 104 down to the carbon nanotube 103. The bottom of the nanochannel 105 is the carbon nanotube 103 (itself) at an isolated location that exposes the carbon nanotube 103 (as discussed further herein). The height of the nanochannel 105 is the thickness of the insulating film 104 deposited on the carbon nanotube 103. For example, the thickness of the insulating film 104 deposited on the carbon nanotube 103 may be controlled to be 1 to 2 nanometers (nm), such that the depth/height of the nanochannel 105 is correspondingly 1 to 2 nm. The nanochannel 105 may be fabricated by standard semiconductor technology, such as, e.g., e-beam lithography, helium ion microscope, etc.

Figure 1D:
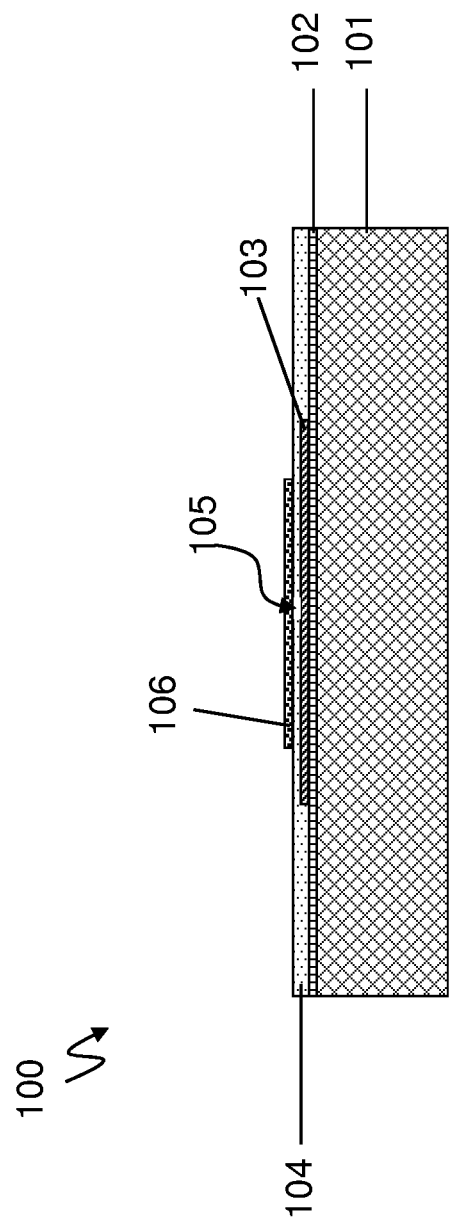

FIG. 1D illustrates an electrically insulating film 106 deposited on the insulating film 104 to seal the nanochannel 105. The micro contact printing (as film transfer) may be employed to fabricate the electrically insulating film 106 as understood by one skilled one the art. As one example, the whole piece of electrically insulating film 106 is first formed on other substrates, and then transferred onto the nanochannel 105. So electrically insulating film 106 is placed on the top the nanochannel 105, bonding with the insulating film 104 and sealing nanochannel 105. Accordingly, the electrically insulating film 106 does not fill the inside of the nanochannel 105.

The nanochannel 105 is formed with the carbon nanotube 103 as a bottom portion, the insulating film 104 as the nanochannel 105 sidewalls, and the electrically insulating film 106 as the top of the nanochannel 105. The length of the nanochannel may be 100 nm to several micrometers in length. In one case, the insulating film 106 may be deposited on the insulating film 104 before the nanochannel 105 is formed. In this case, the nanochannel 105 is opened through the insulating film 104 after the insulating film 106 has been deposited.

Figure 1E:
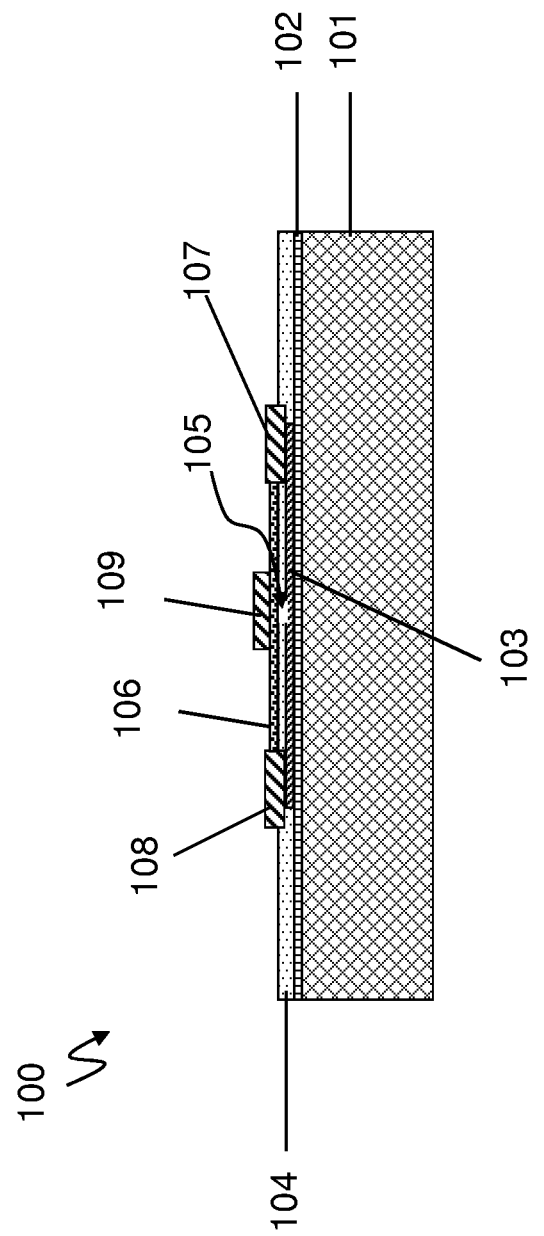

In FIG. 1E, electrodes 107 and 108 are respectively deposited on opposite sides of the carbon nanotube 103. The electrodes 107 and 108 are contacts physically and electrically connected to the carbon nanotube 103. A top electrode 109 is deposited on the electrically insulating film 106. The electrodes 107 and 108 may be metal contacts for the carbon nanotube 103, and the top electrode 109 may be a metal contact (not connected to the carbon nanotube 103). The metal contacts of electrodes 107, 108, and 109 may be any metal such as gold, titanium nitride, etc.

Figure 2A:
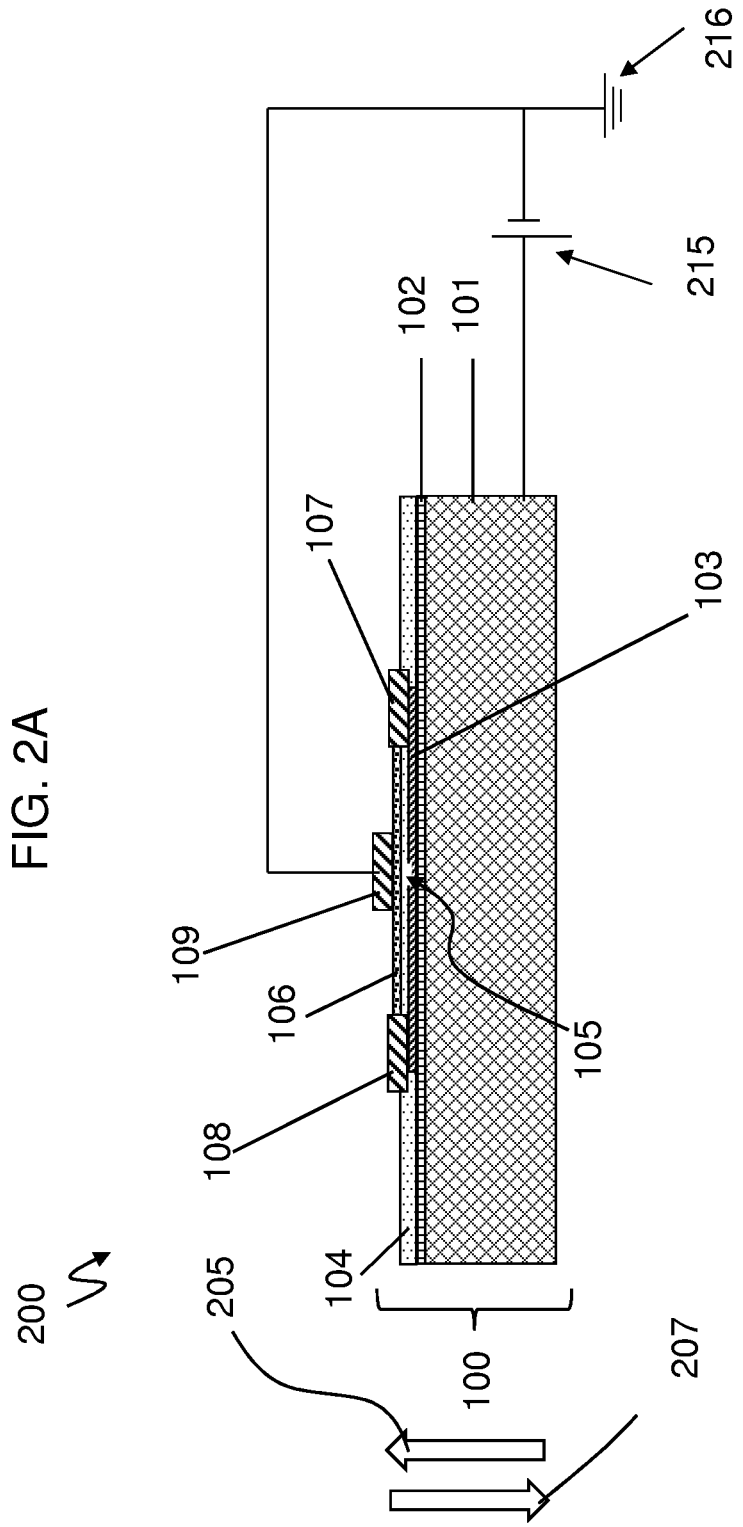
FIG. 2A is a cross-sectional view of an integrated carbon nanotube field effect transistor and nanochannel system according to an embodiment.
Figure 2B:
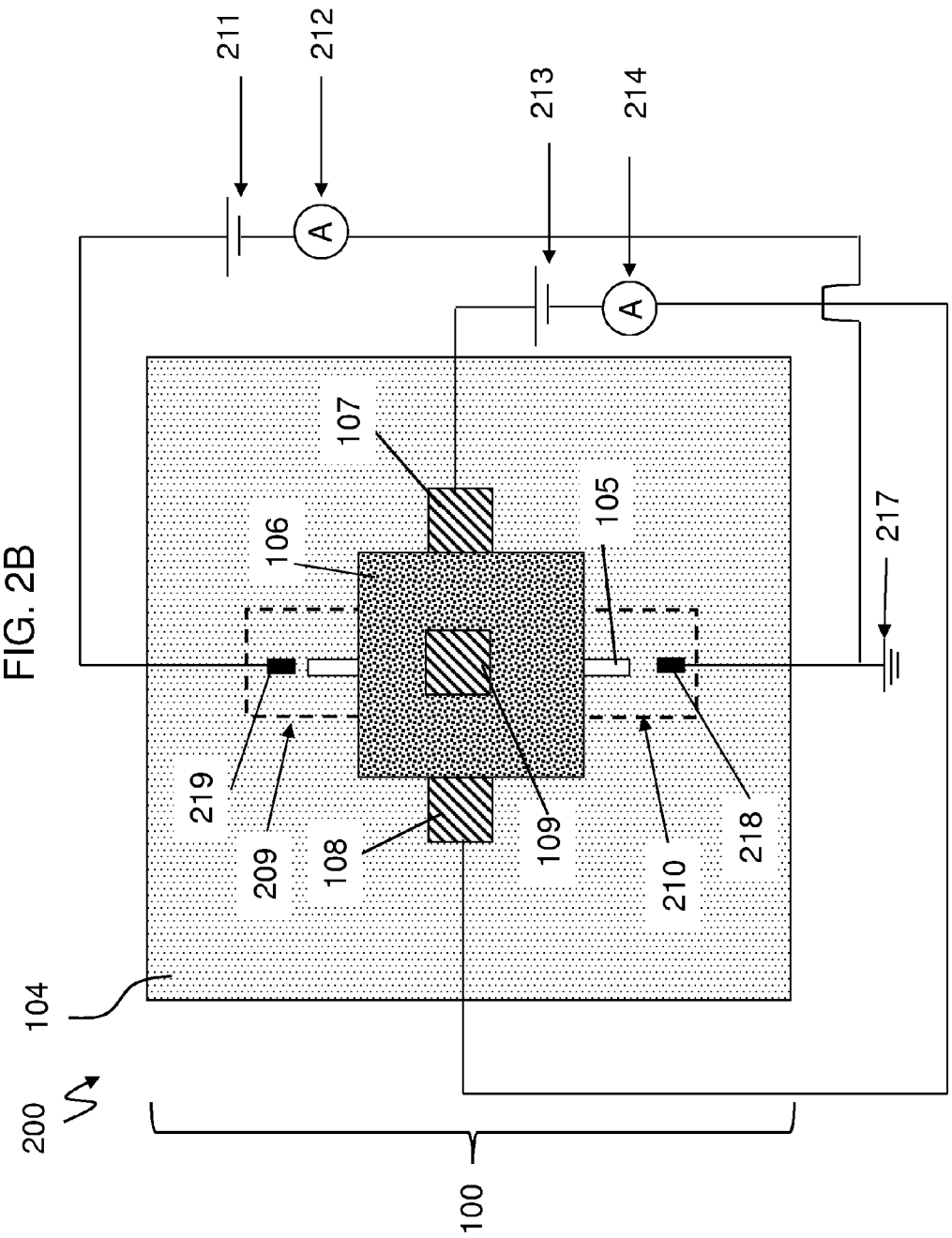
FIG. 2B is a top view the integrated carbon nanotube field effect transistor and nanochannel system according to an embodiment.

FIGS. 2A and 2B illustrate an integrated carbon nanotube field effect transistor and nanochannel system 200 of the device 100 according to an embodiment. FIGS. 2A and 2B may generally be referred to as FIG. 2.

FIG. 2A is a cross-sectional view of the system 200. A voltage source 215 is connected to the substrate 101 and connected to the top electrode 109. The voltage source 215 produces a gate voltage bias for the CNT-FET device 100. The gate voltage bias of the voltage source 215 generates the vertical electrical field 205 between the substrate 101 and top electrode 109, which correspondingly generates downward forces 210 that pull the DNA or RNA inside the nanochannel 105 towards the carbon nanotube 103. The arrows for the vertical electrical field 205 and the downward forces 207 are shown to the left of the figure so as not to obstruct the details, but it is understood that the vertical electrical field 205 and the downward forces 207 are in the device 100. The ground 216 is connected to the negative side of the voltage source 215 and top electrode 109.

FIG. 2B is a top view of the system 200. Inlet 210 and outlet 209 are the locations for an inlet reservoir (with the DNA/RNA molecules as samples to be sequenced) and an outlet reservoir to capture the molecules. The inlet and outlet reservoirs are not shown in FIG. 2 so at not to obscure the figure but are understood by one skilled in the art. The inlet 210 and outlet 209 represent that the two reservoirs have been lifted from the FIG. 2B so that the nanochannel 105 can be viewed. The inlet and outlet reservoirs are respectively sealed at the inlet 210 and outlet 209. The inlet and outlet reservoirs and the nanochannel 105 are filled with a buffer solution. The buffer solution is an electrically conductive electrolyte solution as understood by one skilled in the art. The DNA/RNA sample can be placed into the buffer solution (e.g., introduced into the inlet reservoir) for sensing.

Electrodes 218 and 219 are electrodes that are connected to a voltage source 211 and ammeter 212. The electrodes 218 and 219 may be silver/silver chloride, platinum, etc. DNA (as a target molecule 305 shown in FIG. 3) will be pulled through the nanochannel 105 by the electrical field generated by voltage of the voltage source 211. The ammeter 212 can monitor/measure the ionic current change through the nanochannel 105 when the DNA or RNA is captured and driven inside the nanochannel 105. The change (e.g., drop) in ionic current when the target molecule is in the nanochannel 105, lets the operator (or computer 500 in FIG. 5) know that the target molecule is present.

The positive side of a voltage source 213 may be connected to electrode 107 (as the source) and the negative side of the voltage source 213 may be connected to the electrode 108 (as the drain), voltage source 213 produces the voltage for the CNT-FET device 100. Ammeter 214 monitors/measures the source-drain current (i.e., transistor current) through the carbon nanotube 103 (e.g., from electrode 107 to electrode 108) in the CNT-FET device 100 which can detect nucleotide information (based on the change in source-drain current (i.e., transistor current)) when the DNA/RNA passes over (and touches) the carbon nanotube 103 inside nanochannel 105. The negative voltage applied to the top electrode 109 also pushes the negatively charged DNA molecule to the carbon nanotube 103 for base sensing at a specific bottom location of the nanochannel 105 at which the carbon nanotube 103 is exposed.

When no target molecule is in the nanochannel 105, a baseline current curve (e.g., measured by ammeter 214) is established by a voltage sweep of the voltage source 213 (e.g., for voltages 1-5) to generate a baseline voltage versus current curve for the transistor. For example, the voltage of voltage source 213 is applied to the electrodes 107 and 108 and the transistor current is measured by ammeter 214. From a conventional current flow, current flows from voltage source 213, into electrode 107, through the carbon nanotube 103 (e.g., through the metallic shell), out through the electrode 108, into ammeter 214 (for transistor current measurement), and into the negative side of the voltage source 213.

Also, a baseline (nucleotide) current is established for each base such as base A, base G, base C, and base T for a DNA molecule by individually introducing a (previously) known base into the system 200 for testing to obtain the transistor current unique to each base. As one example case, only base A is introduced into the inlet reservoir at inlet 210. When base A is pulled into the nanochannel 105 by the voltage of voltage source 211 (e.g., the force of the electric field and the force of the negative polarity of the electrode 218 pushing the negatively charged DNA molecule), the base A interacts with (e.g., touches) the carbon nanotube 103 at a specific bottom location 310 (hole/via) of the nanochannel 105 as shown in FIG. 3B. The charges on the base A (in this example) will cause a transfer of charges to the electrical current carriers flowing on the carbon nanotube 103. This will cause the electrical current (measured by the ammeter 214) on the carbon nanotube 103 to change (e.g., drop or increase) as the base A touches the carbon nanotube 103 at the specific bottom location 310 of the nanochannel 105. This process individually occurs for base A, G, C, and T to establish a transistor current baseline, and the respective electrical current change (e.g., the magnitude and time duration of the change) is measured and recorded for each of the respective bases A, G, C, and T. The respective transistor current change (e.g., drop in electrical current for a particular time duration) is used to compare against and identify bases on a target molecule that needs to be sequenced.

Once the system 200 is flushed (as understood by one skilled in the art), the target molecule 305 to be tested is introduced into the inlet reservoir at the inlet 210. The voltage of voltage sources 211, 213, and 215 are all turned on (and remain on during testing). By the voltage of voltage source 211 (i.e., electric voltage potential via electrodes 218 and 219 in the respective inlet and outlet reservoirs), the electric field (not shown) and negative polarity (of electrode 218 push) translocates (moves) the target molecule into (and through) the nanochannel 105. While in the nanochannel 105, the voltage of voltage source 215 drives/pushes the target molecule (i.e., the backbone) and a single base against (i.e., to touch) the carbon nanotube 103 at the specific bottom location 310. While this single base is touching the carbon nanotube 103 and while the voltage of voltage source 213 is applied, the electrical current changes (i.e., source drain current of the transistor drops or increases for a time duration) while the single base touches the carbon nanotube 103 through the specific bottom location 310 of the nanochannel 105.

Figure 3A:
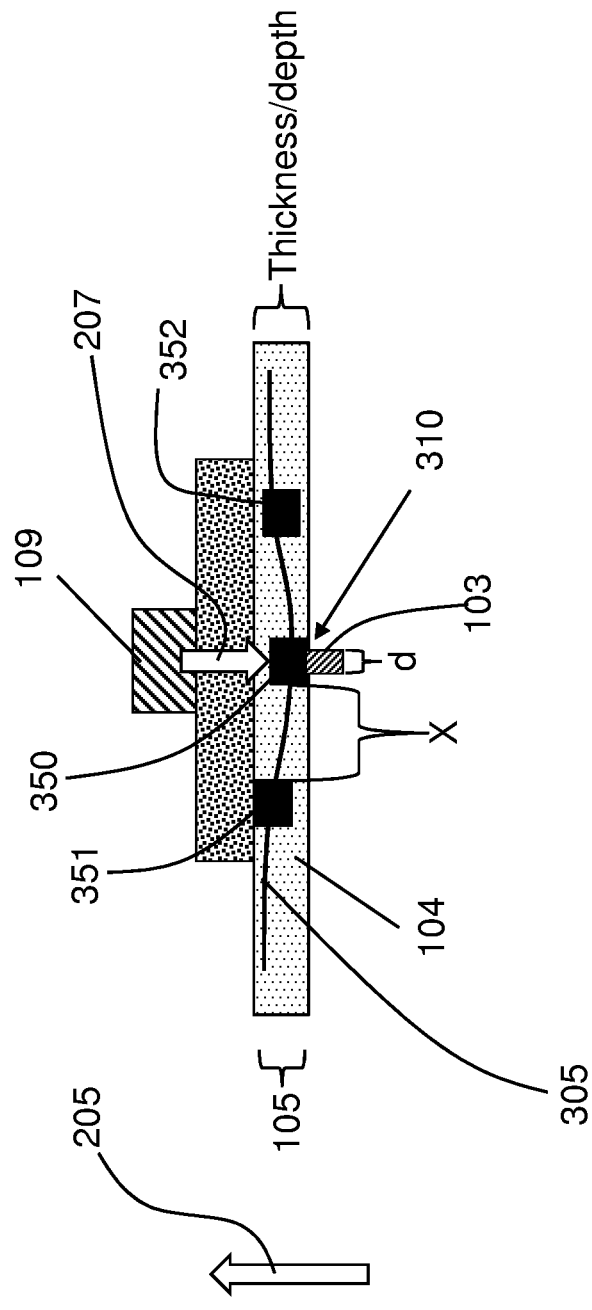
FIG. 3A is an abbreviated version of a cross-sectional view of the carbon nanotube field effect transistor and nanochannel system according to an embodiment.
Figure 3B:
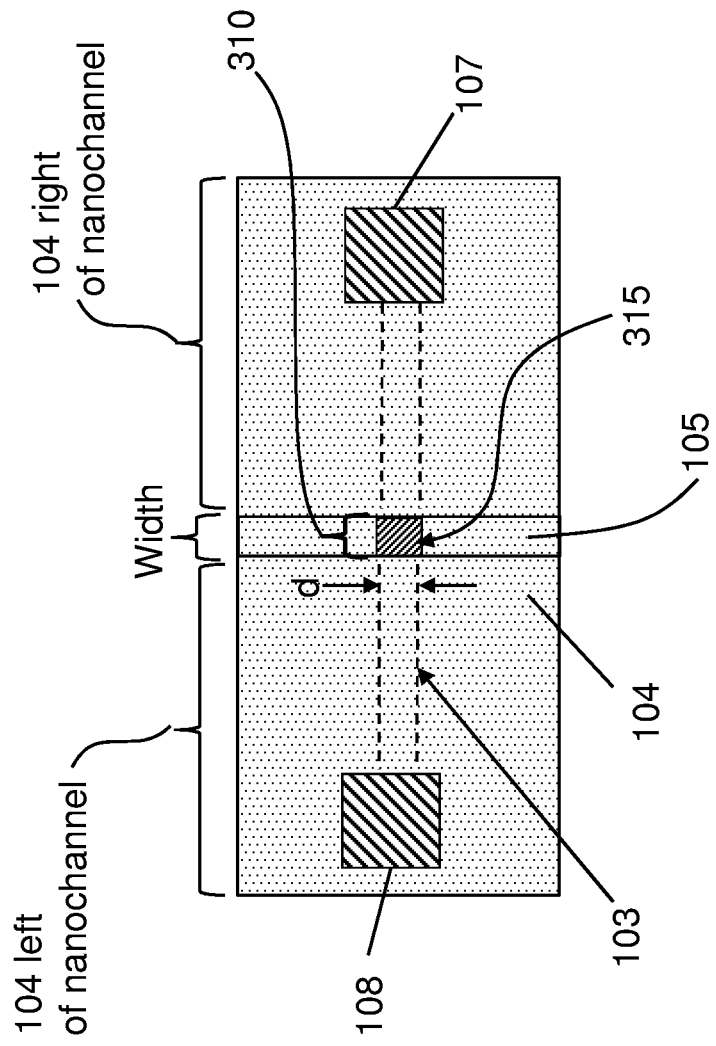
FIG. 3B is an abbreviated version of a top view of the carbon nanotube field effect transistor and nanochannel system according to an embodiment.

FIG. 3A illustrates an abbreviated version of a cross-sectional view of the system 200 with the carbon nanotube field effect transistor (CNT-FET) and nanochannel device 100. So as not to obscure FIGS. 3A and 3B for the reader, certain elements of the system 200 are omitted but it is understood that the omitted elements are part of the figures as discussed herein. FIG. 3A illustrates how the voltage applied to the top electrode 109 (e.g., gate electrode) drives the target molecule 305 down, by particularly pressing a single base 350 to the carbon nanotube 103 at the specific bottom location 310 of the nanochannel 105. The charges (positive or negative) on this particular base 350 interacts the electrical current (charge carriers) flowing on the carbon nanotube 103, to cause the electrical current to change (drop or increase) when measured by the ammeter 214. The electrical field 205 is shown pointing up (and to the left side of the figure so as not obstruct the figure). The downward forces 210 (including the negative voltage polarity applied to the top electrode 109) are pushing the single base 350 on to (an exposed portion 315 of) carbon nanotube 103, while the other bases such as bases 351 and 352 do not touch the carbon nanotube 103 in the nanochannel 105 (at the same time that the single base 350 touches the carbon nanotube 103). The distance X separating each base of the target molecule 305 (such as DNA or RNA) is greater than "d" half of the diameter of the carbon nanotube 103. As such, this ensures that only a single base of the target molecule 305 touches and interacts with the carbon nanotube 103 at a time, because any two bases are too far apart. As an example, the distance X between the bases may be 0.7 nm while d (half of the diameter of the carbon nanotube) may be 0.5 nm.

Also, the thickness (also referred to as the depth and height) of the nanochannel 105 is narrow compared to the height and size of the bases of the target molecule 305. This narrow thickness provides two benefits. The narrowed thickness of the nanochannel 105 causes the bases (and backbone of the target molecule 305) to frictionally rub the inner surface of the nanochannel 105 as the traverse electric field (of the voltage source 212) advances the target molecule 305 through the nanochannel 105. This friction causes the target molecule 305 to stretch for sequencing/reading. Also, the narrowed thickness of the nanochannel 105 helps to confine the bases of the target molecule 305 so that the bases can touch (exposed portion of) the carbon nanotube 103 at the specific bottom location 310 of the nanochannel 105. The diameter of single-stranded DNA is about 1 nm. In order to physically stretch the single-stranded DNA 305, the thickness of the nanochannel 105 should be around 2 nm. The gap is about 1 nm between the carbon nanotube 103 and the top cover 106. So the single strand DNA can be stretched by the physical size of nanochannel 105 when the single strand DNA 305 is pulled through the nanochannel 105 by the electrical field between two electrodes 218 and 219.

This process of reading the bases of the target molecule 305 occurs for each of the bases, and the change in electrical current (i.e., transistor current flowing over carbon nanotube 103) when each individual base touches the carbon nanotube 103 is respectively measured (by ammeter 214) and recorded for each base (e.g., by the computer 500). Accordingly, the change in electrical current (and time duration) is used to compare against (and match) the baseline change in electrical current for each of the respective bases A, G, C, and T (measured at the onset). For example, the change in electrical current for the known bases previously measured may have shown that the baseline current amplitude of base A dropped to amplitude A at 2 volts, the baseline current amplitude of base G dropped to amplitude G at 2 volts, the baseline current amplitude of base C dropped to amplitude C at 2 volts, and the baseline current amplitude of base T dropped to amplitude T (e.g., at 2 volts applied by the voltage source 213). These baseline electrical currents for the known bases are compared against the amplitude measured for the individual (unknown) bases of the target molecule 305 (e.g., at 2 volts applied by the voltage source 213).

FIG. 3B illustrates an abbreviated version of the system 200 from a top view. Particularly, top electrode 109 and the top sealing layer (i.e., electrically insulating 106) of the nanochannel 105 have been lifted off to show the nanochannel 105. FIG. 3B shows the exposed portion 315 of the carbon nanotube 103 through the bottom location 310 of the nanochannel 105. This exposed portion 315 of the carbon nanotube 103 touches and interacts with the single base 350 (which represents any individual base) of the target molecule 305 at a time. The exposed portion 315 of the carbon nanotube 103 may be 1 nm (nanometer), which is the diameter d of the carbon nanotube 103. The width of the exposed portion 315 is the width of the nanochannel 105. The width of nanochannel 105 can be 1 to 2 nm, which can help to linearize the single-stranded DNA. The 1 nm diameter of the carbon nanotube 103 of the exposed portion 315 only allows one base of the target molecule to touch the exposed portion 315 at any time.

In FIG. 3B, the dashed lines show that the carbon nanotube 103 runs underneath the electrically insulating material/film 104 and that the carbon nanotube 103 electrically connects to the electrodes 107 and 108. Also, the dashed lines show that the carbon nanotube 103 is not electrically connectable for interaction except at the exposed portion 315.

FIGS. 4A and 4B are a method 400 for base recognition in an integration of a transistor and a nanochannel system 200 according to an embodiment. Reference can be made to FIGS. 1-3 and 5.

A target molecule (e.g., the target molecule 305) is forced down to (touch) the carbon nanotube 103 a single base at a time in a nanochannel 105 at block 405. The target molecule 305 is forced to the carbon nanotube 103 by applying a gate voltage (by voltage source 213) to the top electrode 109 of the transistor, by a narrow thickness of the nanochannel 105, or both by applying the gate voltage to the top electrode 109 of the transistor and by the narrow thickness of the nanochannel 105.

At block 410, the nanochannel 105 has been patterned over the carbon nanotube 103 to expose the exposed portion 315 of the carbon nanotube 103 at a bottom wall of the carbon nanotube 103, and the top electrode 109 of the transistor is positioned over the exposed portion 315 of the carbon nanotube 103 up through nanochannel 105.

At block 415, the exposed portion 315 of the carbon nanotube 103 is smaller than a separating distance (e.g., distance X) between bases on the target molecule 305, and the exposed portion 315 of the carbon nanotube 103 is configured (with a size) to only accommodate a single base (e.g., base 350) at a time.

The target molecule 305 is stretched by the narrow thickness of the nanochannel 105 and by applying a traverse voltage (by the voltage source 211) across a length direction (e.g., from the inlet 210 to the outlet 219) of the nanochannel 105 between a first electrode (e.g., electrode 218) and a second electrode (e.g., electrode 219) at opposite ends of the nanochannel 105 in the length direction at block 420.

At block 425, the target molecule 305 is frictionally restricted by the narrow thickness (and/or width) of the nanochannel 105 causing the target molecule to stretch as the target molecule 305 restrictedly translocates in the length direction while the traverse voltage is applied.

A transistor current (when voltage of voltage source 213 is applied) is measured (by the ammeter 214) while the single base of the target molecule 305 is forced down to (touch) the exposed portion 315 of the carbon nanotube 103 in the nanochannel 105, such that the single base affects the transistor current (e.g., causes the electrical current to drop or increase) at block 430.

At block 435, an identity (such as base A, G, C, and T) of the single base (e.g., base 350) is determined according to a change in the transistor current while the single base is forced down to the exposed portion 315 of the carbon nanotube 103 in the nano channel 105.

Further, the method includes that when the target molecule is negatively charged the gate voltage applied by the voltage source 215 is negative. When the target molecule is positively charged the gate voltage the voltage source 215 is positive. Particularly, the gate voltage of the top electrode (and to the body of the substrate 101) generates a downward force 207 through the nanochannel 105 above the exposed portion 315, and the downward force 207 presses the target molecule down to touch (only) the exposed portion 315 of the carbon nanotube (while other bases do not touch the exposed portion 315). When the single base is over the carbon nanotube 103, the downward force 207 presses the single base to touch the exposed portion 315 of the carbon nanotube 103 to sense the identity of the single base.

The target molecule 305 is deoxyribonucleic acid or ribonucleic acid. The nanochannel 105 is formed of an insulating material 104 except at the exposed portion 315 of the carbon nanotube 103. Wherein the nanochannel 105 has a thickness (or depth) that is less than a thickness of the insulating material 104 because the insulating material 104 is deposited on both the carbon nanotube 103 and the insulating material 102 layer underneath carbon nanotube.

The thickness (depth) of the nanochannel 105 is (substantially) between 1 to 2 nanometers when the target molecule 305 is a singe strand polynucleotide in order for the target molecule 305 to be stretched as it bumps/slides against the walls of the nanochannel 105. The thickness of the nanochannel 105 is (substantially) between 2 to 4 nanometers when the target molecule 305 is a double strand polynucleotide in order for the target molecule to be stretched.

Also, the thickness of the nanochannel 105 is determined by the diameter of the target molecule to be sequenced in order for the target molecule to be frictionally restricted when translocating through the nanochannel 105.

The traverse voltage (applied by the voltage source 211) is substantially between 0 to 5 volts. The gate voltage (applied by the voltage source 215) is substantially between −10 to 0 volts when the target molecule 305 is negatively charged. The gate voltage (applied by the voltage source 215) is substantially between 0 to +10 volts when the target molecule is positively charged.

A coating molecule is applied to the carbon nanotube 103 (e.g., at least at the exposed portion 315) to increase sensitivity of the transistor to accept charges from the single base 350 being pressed to the exposed portion 315. The coating molecule increases a selectivity of bases of the target molecules which may cause certain bases to attach to the exposed portion 315. As one example, the coating molecule can be 11-mercaptoundecanol, which can be switched based on the polarity by the external voltage (of the voltage source 213). The coating molecule can help to trap and sense the single base when the voltage is positive.

The transistor comprises a source electrode (e.g., electrode 107) and a drain electrode (e.g., electrode 108) connected by the carbon nanotube 103, and wherein the transistor current flows from the source electrode to the drain electrode through the carbon nanotube 103.

Figure 5:
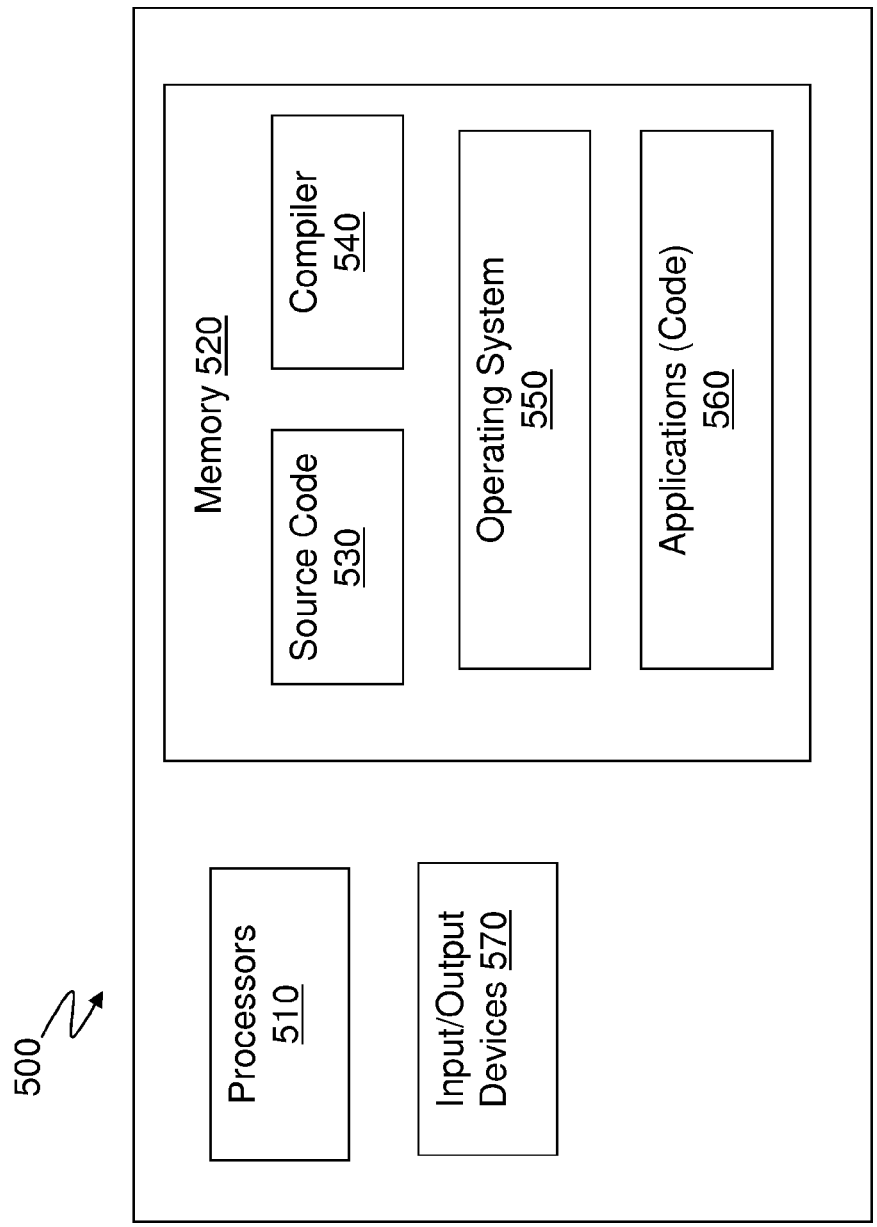
FIG. 5 is a block diagram that illustrates an example of a computer (computer test setup) having capabilities, which may be included in and/or combined with embodiments.

FIG. 5 illustrates an example of a computer 500 (e.g., as part of the computer test setup for testing and analysis) which may implement, control, and/or regulate the respective voltages of the voltage sources, respective measurements of the ammeters, and display screens for displaying various current amplitude (amplitude versus dwell (duration) time graphs for the applied voltage) as discussed herein. The computer 500 also stores the respective electrical current amplitudes of each base tested and measured to be compared against the baselines current amplitudes of different bases.

Various methods, procedures, modules, flow diagrams, tools, applications, circuits, elements, and techniques discussed herein may also incorporate and/or utilize the capabilities of the computer 500. Moreover, capabilities of the computer 500 may be utilized to implement features of exemplary embodiments discussed herein. One or more of the capabilities of the computer 500 may be utilized to implement, to connect to, and/or to support any element discussed herein (as understood by one skilled in the art) in FIGS. 1-4. For example, the computer 500 which may be any type of computing device and/or test equipment (including ammeters, voltage sources, current meters, connectors, etc.). Input/output device 570 (having proper software and hardware) of computer 500 may include and/or be coupled to the nanodevices and structures discussed herein via cables, plugs, wires, electrodes, patch clamps, etc. Also, the communication interface of the input/output devices 570 comprises hardware and software for communicating with, operatively connecting to, reading, and/or controlling voltage sources, ammeters, and current traces (e.g., magnitude and time duration of current), etc., as discussed herein. The user interfaces of the input/output device 570 may include, e.g., a track ball, mouse, pointing device, keyboard, touch screen, etc., for interacting with the computer 500, such as inputting information, making selections, independently controlling different voltages sources, and/or displaying, viewing and recording current traces for each base, molecule, biomolecules, etc.

Generally, in terms of hardware architecture, the computer 500 may include one or more processors 510, computer readable storage memory 520, and one or more input and/or output (I/O) devices 570 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 510 is a hardware device for executing software that can be stored in the memory 520. The processor 510 can be virtually any custom made or commercially available processor, a central processing unit (CPU), a data signal processor (DSP), or an auxiliary processor among several processors associated with the computer 500, and the processor 510 may be a semiconductor based microprocessor (in the form of a microchip) or a macroprocessor.

The computer readable memory 520 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 520 may incorporate electronic, magnetic, optical, and/or other types of storage media. Note that the memory 520 can have a distributed architecture, where various components are situated remote from one another, but can be accessed by the processor 510.

The software in the computer readable memory 520 may include one or more separate programs, each of which comprises an ordered listing of executable instructions for implementing logical functions. The software in the memory 520 includes a suitable operating system (O/S) 550, compiler 540, source code 530, and one or more applications 560 of the exemplary embodiments. As illustrated, the application 560 comprises numerous functional components for implementing the features, processes, methods, functions, and operations of the exemplary embodiments.

The operating system 550 may control the execution of other computer programs, and provides scheduling, input-output control, file and data management, memory management, and communication control and related services.

The application 560 may be a source program, executable program (object code), script, or any other entity comprising a set of instructions to be performed. When a source program, then the program is usually translated via a compiler (such as the compiler 540), assembler, interpreter, or the like, which may or may not be included within the memory 520, so as to operate properly in connection with the O/S 550. Furthermore, the application 560 can be written as (a) an object oriented programming language, which has classes of data and methods, or (b) a procedure programming language, which has routines, subroutines, and/or functions.

The I/O devices 570 may include input devices (or peripherals) such as, for example but not limited to, a mouse, keyboard, scanner, microphone, camera, etc. Furthermore, the I/O devices 570 may also include output devices (or peripherals), for example but not limited to, a printer, display, etc. Finally, the I/O devices 570 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 570 also include components for communicating over various networks, such as the Internet or an intranet. The I/O devices 570 may be connected to and/or communicate with the processor 510 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 560 is implemented in hardware, the application 560 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method for base recognition in an integration of a transistor and a nanochannel, the method comprising:

forcing a target molecule down to a carbon nanotube a single base at a time in the nanochannel, the target molecule being forced to the carbon nanotube by applying a gate voltage to a top electrode of the transistor, by a narrow thickness of the nanochannel, or both by applying the gate voltage to the top electrode of the transistor and by the narrow thickness of the nanochannel;

wherein the nanochannel having been patterned over the carbon nanotube exposes an exposed portion of the carbon nanotube at a bottom wall of the carbon nanotube, the top electrode of the transistor positioned over the exposed portion of the carbon nanotube through the nanochannel;

wherein the exposed portion of the carbon nanotube is smaller than a separating distance between bases on the target molecule, the exposed portion of the carbon nanotube being configured to only accommodate the single base at a time;

stretching the target molecule by the narrow thickness of the nanochannel and by applying a traverse voltage across a length direction of the nanochannel between a first electrode and a second electrode at opposite ends of the nanochannel in the length direction;

wherein the target molecule is frictionally restricted by the narrow thickness of the nanochannel causing the target molecule to stretch as the target molecule restrictedly translocates in the length direction while the traverse voltage is applied;

measuring a transistor current while the single base of the target molecule is forced down to the exposed portion of the carbon nanotube in the nanochannel, the single base affecting the transistor current; and determining an identity of the single base according to a change in the transistor current while the single base is forced down to the exposed portion of the carbon nanotube in the nanochannel.

2. The method of claim 1, wherein when the target molecule is negatively charged the gate voltage is negative.

3. The method of claim 1, wherein when the target molecule is positively charged the gate voltage is positive.

4. The method of claim 1, wherein the gate voltage of the top electrode generates a downward force through the nanochannel above the exposed portion, the downward force pressing the target molecule down to touch the exposed portion of the carbon nanotube.

5. The method of claim 4, wherein when the single base is over the carbon nanotube, the downward force presses the single base to touch the exposed portion of the carbon nanotube to sense the identity of the single base.

6. The method of claim 1, wherein the target molecule is deoxyribonucleic acid or ribonucleic acid.

7. The method of claim 1, wherein the nanochannel is formed of an insulating material except at the exposed portion of the carbon nanotube.

8. The method of claim 7, wherein the nanochannel has a thickness that is less than a thickness of the insulating material.

9. The method of claim 1, wherein a thickness of the nanochannel is substantially between 1 to 2 nanometers when the target molecule is a singe strand polynucleotide in order for the target molecule to be stretched.

10. The method of claim 1, wherein a thickness of the nanochannel is substantially between 2 to 4 nanometers when the target molecule is a double strand polynucleotide in order for the target molecule to be stretched.

11. The method of claim 1, wherein a thickness of the nanochannel is determined by a diameter of the target molecule to be sequenced in order for the target molecule to be frictionally restricted when translocating through the nanochannel.

12. The method of claim 1, wherein the traverse voltage is substantially between 0 to 5 volts.

13. The method of claim 1, wherein the gate voltage is substantially between −10 to 0 volts when the target molecule is negatively charged.

14. The method of claim 1, wherein the gate voltage is substantially between 0 to +10 volts when the target molecule is positively charged.

15. The method of claim 1, wherein a coating molecule is applied to the carbon nanotube to increase sensitivity of the transistor;
   wherein the coating molecule increases a selectivity of bases of the target molecule.

16. The method of claim 1, wherein the transistor comprises a source electrode and a drain electrode connected by the carbon nanotube;
   wherein the transistor current flows from the source electrode to the drain electrode through the carbon nanotube.

* * * * *